(12) United States Patent
Saadat et al.

(10) Patent No.: US 8,460,181 B2
(45) Date of Patent: Jun. 11, 2013

(54) EPICARDIAL ACCESS AND TREATMENT SYSTEMS

(75) Inventors: Vahid Saadat, Atherton, CA (US); Ruey-Feng Peh, Mountain View, CA (US); Edmund Tam, Mountain View, CA (US)

(73) Assignee: Nidus Medical, LLC, Atherton, CA (US)

( * ) Notice: Subject to any disclaimer, the term of this patent is extended or adjusted under 35 U.S.C. 154(b) by 1060 days.

(21) Appl. No.: 12/355,378

(22) Filed: Jan. 16, 2009

(65) Prior Publication Data
US 2009/0187074 A1  Jul. 23, 2009

Related U.S. Application Data

(60) Provisional application No. 61/021,839, filed on Jan. 17, 2008.

(51) Int. Cl.
*A61B 1/00* (2006.01)
*A61B 1/04* (2006.01)

(52) U.S. Cl.
USPC .............................. 600/129; 600/130; 396/17

(58) Field of Classification Search
USPC .............. 396/14, 17; 600/129, 101, 114, 116, 600/127, 130, 148
See application file for complete search history.

(56) References Cited

U.S. PATENT DOCUMENTS

| | | | | |
|---|---|---|---|---|
| 3,874,388 A * | 4/1975 | King et al. | | 606/232 |
| 3,882,852 A * | 5/1975 | Sinnreich | | 600/104 |
| 4,957,486 A * | 9/1990 | Davis | | 604/102.02 |
| 5,575,810 A * | 11/1996 | Swanson et al. | | 607/99 |
| 6,235,044 B1 * | 5/2001 | Root et al. | | 606/200 |
| 6,277,066 B1 * | 8/2001 | Irwin | | 600/115 |
| 6,306,081 B1 * | 10/2001 | Ishikawa et al. | | 600/127 |
| 7,063,693 B2 * | 6/2006 | Guenst | | 606/1 |
| 7,398,781 B1 * | 7/2008 | Chin | | 128/898 |
| 7,487,780 B2 | 2/2009 | Hooven | | |
| 2004/0097788 A1 * | 5/2004 | Mourlas et al. | | 600/116 |
| 2004/0138527 A1 * | 7/2004 | Bonner et al. | | 600/114 |
| 2005/0075662 A1 * | 4/2005 | Pedersen et al. | | 606/194 |
| 2005/0090846 A1 * | 4/2005 | Pedersen et al. | | 606/159 |
| 2005/0096502 A1 * | 5/2005 | Khalili | | 600/106 |
| 2005/0250983 A1 * | 11/2005 | Tremaglio et al. | | 600/101 |
| 2006/0025800 A1 | 2/2006 | Suresh | | |
| 2006/0184048 A1 * | 8/2006 | Saadat | | 600/478 |
| 2007/0083082 A1 | 4/2007 | Kiser et al. | | |
| 2007/0167828 A1 * | 7/2007 | Saadat | | 600/463 |
| 2007/0185386 A1 * | 8/2007 | Cheng | | 600/179 |
| 2008/0058590 A1 * | 3/2008 | Saadat et al. | | 600/109 |
| 2009/0062871 A1 | 3/2009 | Chin et al. | | |
| 2009/0062872 A1 | 3/2009 | Chin et al. | | |
| 2009/0171301 A1 * | 7/2009 | Becker | | 604/264 |

* cited by examiner

*Primary Examiner* — Clayton E LaBalle
*Assistant Examiner* — Warren K Fenwick
(74) *Attorney, Agent, or Firm* — Levine Bagade Han LLP

(57) ABSTRACT

Epicardial access and treatment systems are described herein where such devices may utilize multiple expanding frame members coupled to a flexible or rigid deployment catheter shaft. The multiple frame members may extend distally to collapse into a low-profile configuration and may further expand or open radially to create a working or surgical field under direct visualization and defined by the frame members and surrounding membrane while retracting any surrounding tissue. Moreover, the distal ends of each frame member may be tapered such that the frame members may close tightly relative to one another forming an atraumatic end. Any number of therapeutic tools can be passed through the catheter for performing any number of procedures on the tissue.

9 Claims, 17 Drawing Sheets

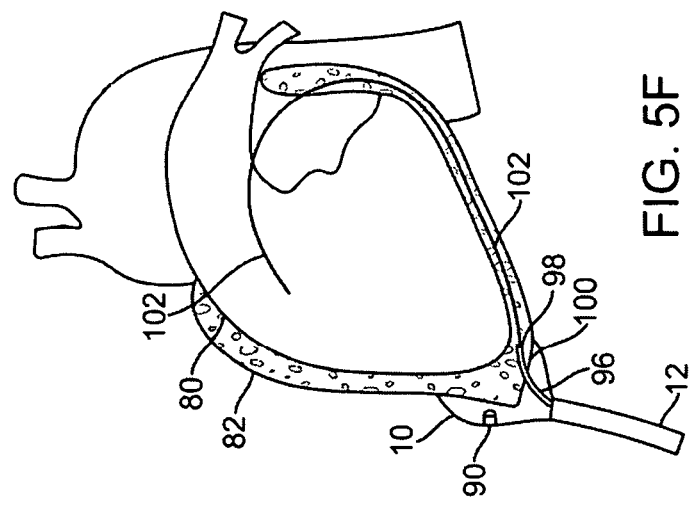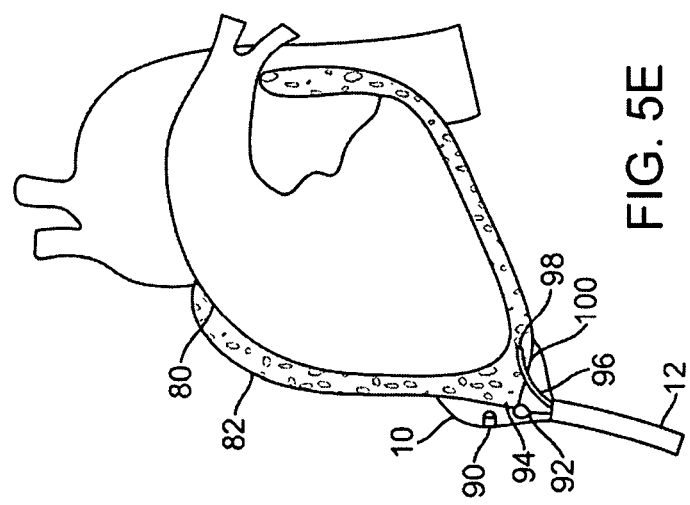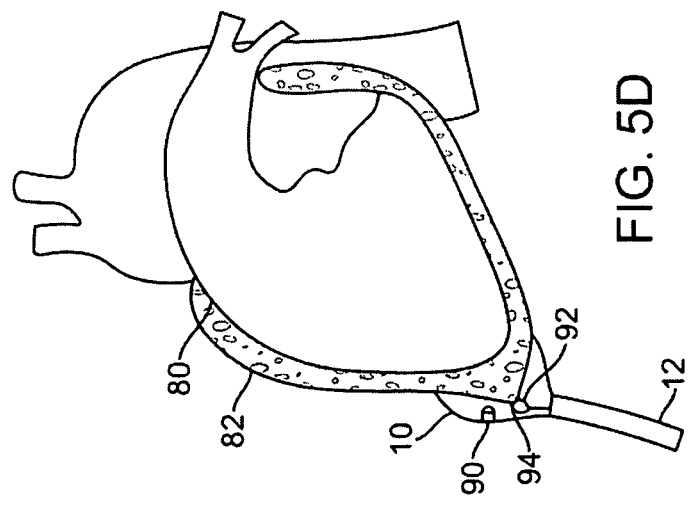

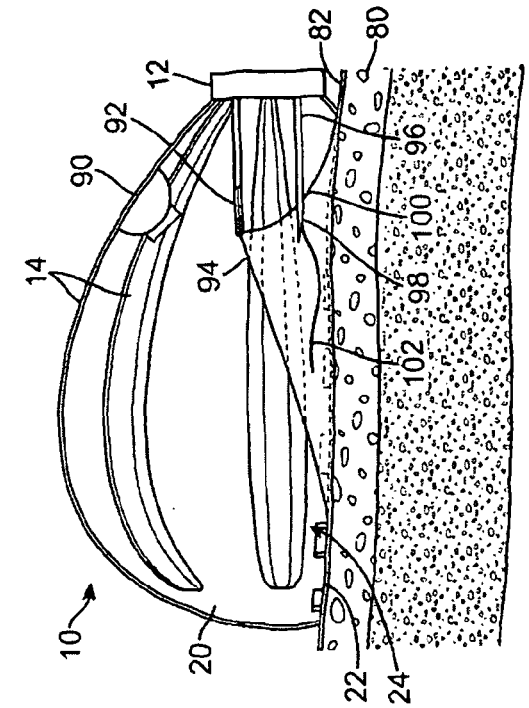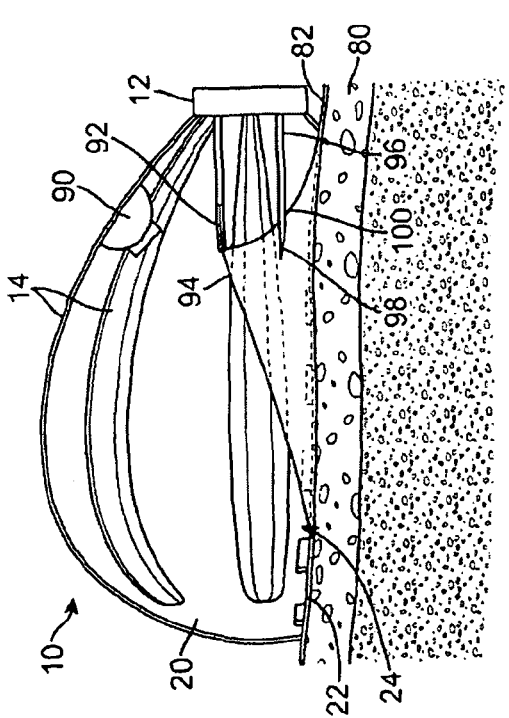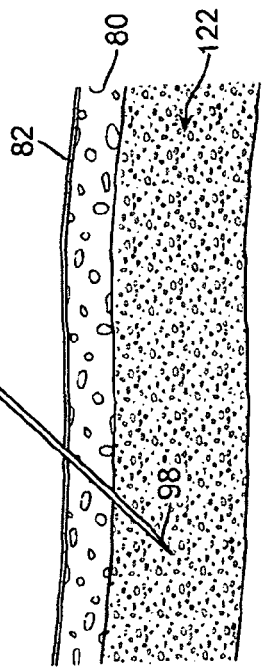
FIG. 8D
FIG. 8E
FIG. 8C

EPICARDIAL ACCESS AND TREATMENT SYSTEMS

CROSS-REFERENCE TO RELATED APPLICATIONS

This application claims the benefit, of priority to U.S. Prov. Pat. App. 61/021,839 filed Jan. 17, 2008, which is incorporated herein by reference in its entirety.

FIELD OF THE INVENTION

The present invention relates generally to medical devices used for accessing, visualizing and/or treating regions of epicardial tissue within the pericardium. More particularly, the present invention relates to instruments having a reconfigurable frame for accessing epicardial tissue and treating the tissue within a stable working theater while under direct visualization.

BACKGROUND OF THE INVENTION

In treating organs such as the heart, access by surgeons have typically involved an invasive procedure such as a sternotomy, thoracotomy, as well as subxiphoid incisions along with retraction of the sternum to expose the anterior pericardium. Such procedures are typically employed to dislodge the heart to provide access to various regions of the heart tissue. Moreover, procedures such as thoracotomies may additionally require the deflation of one or both lungs to provide the necessary access. However, because of their invasive nature, such procedures are not desirable.

Minimally invasive surgeries may employ small, access incisions or utilize ports, yet because such procedures are typically employed while under the direct vision of the surgeon, fairly large incisions are still utilized to provide the surgeon a direct view of the surgical field. Other minimally invasive procedures have utilized endoscopic devices and instruments which are introduced within the thoracic cavity via one or more ports positioned within the intercostal spaces. However, such methods fail to allow access to all regions of the heart by the surgeon.

Moreover, other conventional procedures, whether open heart surgery or minimally invasive surgery, typically require a relative large incision in the pericardium to expose the heart. As the heart typically underlies the pericardium, incising the pericardial sac without inadvertently damaging the heart tissue is typically handled by creating a second incision into the thoracic cavity. A separate instrument, such as graspers or forceps, is introduced into the chest to pull the pericardium away from the heart to allow for an incision to be made into the pericardial sac. However, this requires multiple incisions to be made into the patient and the advancement of multiple instruments in separate passageways.

Such incisions through the pericardium are desirably left as small as possible to reduce fibrous adhesions to the heart. Thus, dilating instruments are desirably as small as possible to minimize any trauma to the tissue. However, typical dilators such as balloon dissectors exert shear forces on the surrounding tissue as they are advanced in the body.

Thus, it is desirable to provide apparatus and methods which provide for relatively safe and minimally invasive access to all regions of the heart in an atraumatic manner while under direct visualization without having to provide additional incisions into the patient body.

BRIEF SUMMARY OF THE INVENTION

A device utilized for retracting tissue and forming a working or surgical, theater within the body may generally comprise an expandable frame or structure which reconfigures to define the working or surgical theater within the body without the need for additional instrumentation. Such a device may provide a platform for minimally invasive treatments to be carried out for a variety of procedures while under direct visualization via an imager (e.g., CMOS, CCD, optical fiber, etc.) within the working or surgical theater.

A reconfigurable frame assembly may extend from a distal end of a flexible catheter such that segmented frame members may be collapsed into a low-profile configuration where the distal ends of each frame member may be tapered such that the frame members close tightly relative to one another forming a tapered portion with an atraumatic or blunted distal end which may also define an optional opening through which a guidewire may pass. The frame assembly may maintain its closed configuration without the aid of a sheath although other variations may utilize a slidable outer sheath to slide over and collapse and/or expand the multi-segmented frame members. Each frame member may be comprised of a rigid body that can be made from any number of materials, e.g., Titanium, stainless steel, or hard plastics such as thermoset plastics, polycarbonate, polyurethane, polysulfone, or other thermoset materials, etc. Alternatively, frame members may be comprised of resilient materials, e.g., shape memory materials (such as Nickel-Titanium alloys or shape memory polymers), which are capable of reconfiguring between its low-profile configuration and its deployed configuration.

A barrier or membrane may extend between the members or it may be attached as a continuous membrane to the members such that a contact edge which defines a lateral opening is formed along a side of frame assembly such that opening is off-axis relative to a longitudinal axis of the catheter. To actuate the frame members to reconfigure into their deployment configuration, the frame members may be biased to conform to its deployment shape (either when formed from a shape memory or superelastic material or other resilient material as previously mentioned) when in a relaxed configuration. Alternatively, one or more tensioning wires or members may be coupled to one or more corresponding frame members such that the proximal actuation of these wires may urge the frame members into their deployed configuration. In yet other variations, the deployment or retraction of the frame members relative to the catheter can be controlled by any number of mechanisms such as pullwires, hydraulics, electric motor-driven gears, cams, linkages, etc. These mechanisms may be incorporated within the elongated catheter and coupled to one or more frame members to control the opening and/or closing.

With the frame assembly deployed into its expanded configuration, each of the frame members may move apart from one another such that the membrane is distended to form a continuous curved, arcuate, or angled shape which defines the working or surgical theater therein. Any number of tools, e.g., RF ablation probe, optical fibers, laser, ultrasound, cryo-ablation probe, microwave ablation probe, graspers, needles, guidewires, illumination bundles, etc., may be advanced through one or more working lumens defined through the catheter and positioned within the working theater to treat the underlying tissue encompassed within the opening. Additionally and/or alternatively, any number of biological or chemical agents (e.g., saline, biological compounds, fluoroscopy contrast/dyes, etc.) may also be introduced through the catheter as well. The interior of the working or surgical theater and the underlying tissue may be visualized directly via a fiberscope or an electronic imager (e.g., CMOS, CCD, etc.) positioned along an interior surface of the frame assembly and angled such that the field of view of the imager encompasses the area defined by the assembly.

The treatment system may additionally incorporate a steerable section along the catheter proximal of frame assembly to provide for articulation of the device when deployed within the patient body. Manipulation of the steerable section may be controlled by the operator externally of the patient by any number of steering mechanisms to curve frame assembly in either a first direction or second direction opposite to the first direction. By optionally incorporating a steerable distal section, the frame assembly in either its low-profile or deployed configuration may be articulated within a plane (e.g., a curved plane) or out-of-plane to position the frame assembly along a curved tissue surface, such as the epicardial surface.

In use, the device may be advanced through a subxiphoid access point to access the thoracic cavity and the heart in particular. Generally, an incision may be made below the xiphoid process overlying the entry site and the linea alba, for instance, may be incised to obtain the subxiphoid access. The device in its low-profile tapered delivery configuration may be introduced through the incision and superiorly into the thoracic cavity until the frame assembly is adjacent to the pericardial sac of the heart. Once desirably positioned, the frame assembly may be deployed into its open configuration and opening may be placed against the exterior surface of the pericardial sac and the tissue may be directly visualized, either via the fiberscope or electronic imager. As the frame assembly is deployed, the surrounding tissue may be retracted by the frame members and the working or surgical theater may be created over the tissue surface.

Once the frame assembly has been deployed over the pericardial tissue, an instrument such as a tissue grasper may be advanced through catheter and into the working theater to grasp a portion of the pericardial tissue to stabilize it. A piercing instrument may then be advanced into the working theater through the catheter and an opening may be created through the pericardial sac. With the opening formed, a guidewire may be advanced, for example, through the piercing instrument and through the pericardial sac into the epicardial space. Once the guidewire has been passed through the opening in the pericardial sac, the piercing instrument may be removed and a dilating instrument may be advanced along the guidewire to dilate the opening. Alternatively, the collapsed frame assembly may be advanced through the pericardial opening to dilate it directly.

Frame assembly may then be collapsed back into its low-profile delivery configuration and advanced along the guidewire and through the dilated pericardial opening until it enters the epicardial space where frame assembly may then be reconfigured back to its deployed configuration. The re-deployment of the frame assembly may retract the pericardial tissue to create the working theater within the epicardial space while directly against the epicardial tissue. The entire procedure may be performed while under the guidance of direct visualization through the fiberscope or electronic imager within the working theater to facilitate the access procedure as well as any subsequent treatments.

In yet another variation, the frame assembly may further include one or more defined suction ports positioned around the opening to facilitate temporary securement or stabilization of the device against the tissue surface despite movement of the tissue such as when the heart beats. Generally, the frame assembly may comprise an attachment portion while the catheter may include a flexible and/or elastic portion to accommodate for the difference in relative movement between the frame assembly and the catheter.

BRIEF DESCRIPTION OF THE DRAWINGS

FIGS. 5A to 5F illustrate an example for accessing the underlying epicardial tissue through the pericardial sac while under direct visualization where a portion of the pericardial sac is grasped and lifted from the epicardial tissue to allow a piercing instrument to pass therethrough and introduce a guidewire between the two layers.

FIGS. 8A to 8D show partial cross-sectional detail views illustrating the engagement of a portion of the pericardial sac and the passage of a piercing instrument through the lifted portion within the surgical field of die device.

FIG. 8E shows a partial cross-sectional view of a piercing instrument introduced through the epicardial tissue and into a chamber of the heart.

DETAILED DESCRIPTION OF THE INVENTION

In performing any number of procedures within or upon a body lumen or body cavity, such as within a heart chamber, peritoneal, or thoracic cavity, etc. of a patient, an instrument having a low-profile configuration for delivery into and/or through a body and an expandable configuration for retracting or moving tissue from a working distal end of the assembly may be utilized. Such a device may generally comprise an expandable frame or structure which reconfigures to define a working or surgical theater within the body without the need for additional instrumentation. Such a device may provide a platform for minimally invasive treatments to be carried out for a variety of procedures while under direct visualization via an imager (e.g., CMOS, CCD, optical fiber, etc.) within the working or surgical theater.

As visualization and deployment of instruments may be provided through the device and contained within the working theater, access and treatment may be effected upon tissue such as the epicardial tissue surface through a minimum number of entry ports into the body. For example, visualization and treatment upon epicardial tissue may be effected through a single device introduced. Into the body via a single subxiphoid access point or more access points if necessary or desired. As the device provides a defined working or surgical theater within the body by retracting any surrounding tissue and containing the visualized working space, the device provides for minimally invasive access potentially over the entire region of the epicardial tissue by additionally providing articulation of the reconfigurable frame assembly.

Moreover, the system utilizing the device may be introduced into different areas of the body for various procedures, e.g., trans-septal access and/or patent foramen ovale closure, cutting of the corrugator muscle and accessing the breast from the navel in cosmetic surgery, placing of neurostimulator leads for pain management, implanting of artificial discs and/or injecting of agents (such as artificial nuclei) to the spine, visualization and treatment of the lungs along a subxiphoid approach, etc.

Figure 1A:
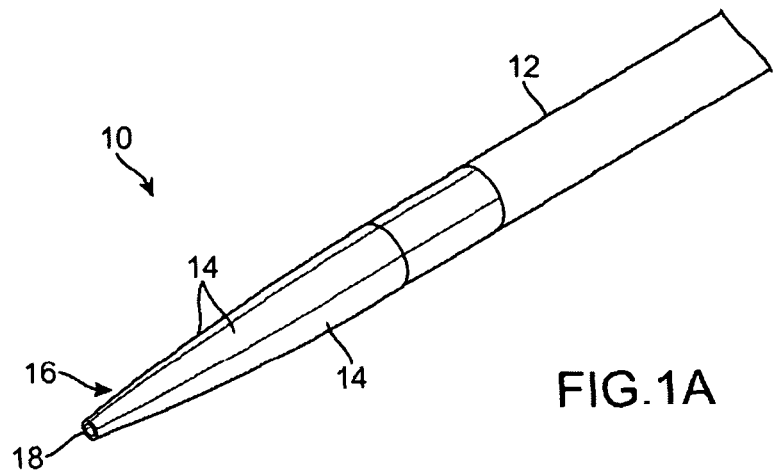
FIGS. 1A to 1C show respective perspective views of one example of an access and treatment device reconfigured from its low-profile configuration to its deployed configuration which defines an open surgical field contained within the device with one or more instruments advanced therethrough.
Figure 1B:
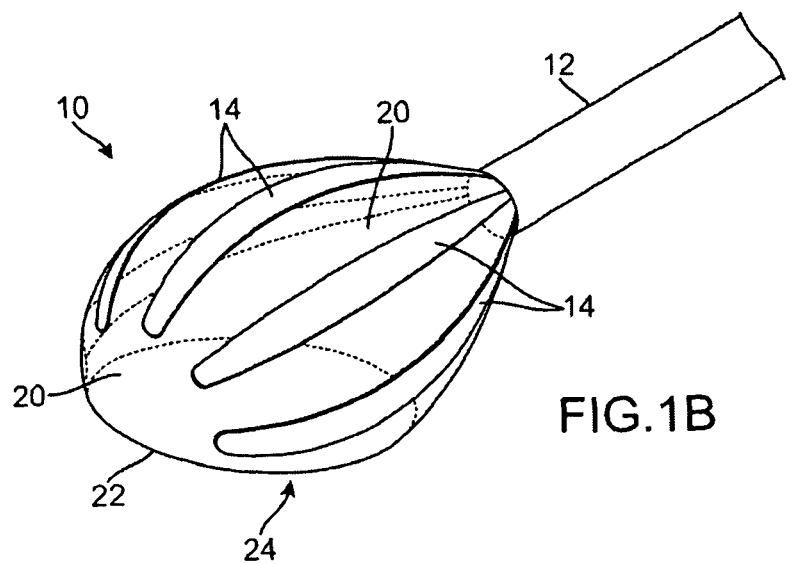
Figure 1C:
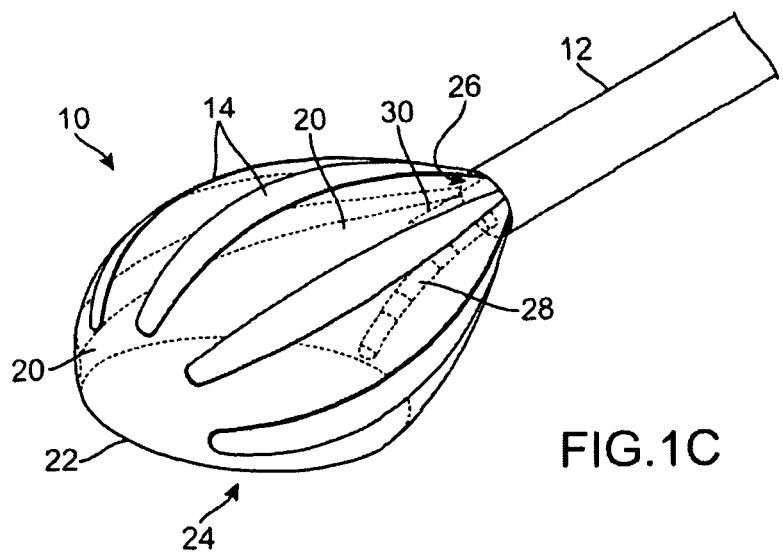

Turning now to FIGS. 1A to 1C, perspective views of one example of an access and treatment device are illustrated where a reconfigurable frame assembly 10 may extend from a distal end of a flexible catheter 12. In other variations, catheter 12 may comprise a rigid elongate shaft. As shown in FIG. 1A, segmented frame members 14 may be collapsed into a low-profile configuration where the distal ends of each frame member 14 may be tapered such that the frame members 14 may close tightly relative to one another forming a tapered portion 16 with an atraumatic or blunted distal end which may also define an optional opening 18 through which a guidewire may pass, as described in further detail below. Although the example illustrates five frame members 14, the number of frame members 14 may vary anywhere from two or more members. Regardless of the number of frame members 14, the members 14 may be configured such that they close collectively in apposition when in the low-profile configuration to present a smooth surface. The frame assembly 10 may maintain its closed configuration without the aid of a sheath although other variations may utilize a slidable outer sheath to slide over and collapse and/or expand the multi-segmented frame members 14. Each frame member 14 may be comprised of a rigid body that can be made from any number of materials, e.g., Titanium, stainless steel, or hard plastics such as thermoset plastics, polycarbonate, polyurethane, polysulfone, or other thermoset materials, etc. Alternatively, frame members 14 may be comprised of resilient materials, e.g., shape memory materials (such as Nickel-Titanium alloys or shape memory polymers), which are capable of reconfiguring between its low-profile configuration and its deployed configuration, as described herein.

As illustrated in FIG. 1B, frame assembly 10 may be actuated to reconfigure from its low-profile configuration in FIG. 1A to its deployed configuration in FIG. 1B where the frame members 14 form an opened configuration, which may be curved or arcuate or even angled. A barrier or membrane 20 may extend between the members 14 or it may be attached as a continuous membrane 20 to the members 14 such that a contact edge 22 which defines a lateral opening 24 is formed along a side of frame assembly 10 such that opening 24 is off-axis relative to a longitudinal axis of catheter 12. To actuate frame members 14 to reconfigure into their deployment configuration, frame members 14 may be biased to conform to its deployment shape (either when formed from a shape memory or superelastic material or other resilient material as previously mentioned) when in a relaxed configuration.

At least a proximal portion of frame members 14 may be translatable relative to catheter 12 such that proximally retracting members 14 (or advancing catheter 12 relative to frame members 14) may urge or bias members 14 into their collapsed configuration relative to one another. The proximal withdrawal of catheter 12 (or distal advancement of members 14) relative to members 14 may un-constrain the frame members 14 such that they are free to conform to their deployed configuration, as shown. Collapsing the frame members 14 from their deployed configuration back to their delivery configuration may be effected by reversing the process such that catheter 12 may be advanced distally (or frame members 14 may be withdrawn proximally) at least partially over a proximal portion of the frame members 14 such that the members 14 collapse into their low-profile shape. Alternatively, one or more tensioning wires or members may be coupled to one or more corresponding frame members 14 such that the proximal actuation of these wires may urge the frame members 14 into their deployed configuration.

In yet other variations, the deployment or retraction of the frame members 14 relative to the catheter 12 can be controlled by any number of mechanisms such as pullwires, hydraulics, electric motor-driven gears, cams, linkages, etc. These mechanisms may be incorporated within the elongated catheter 12 and coupled to one or more frame members 14 to control the opening and/or closing.

With frame assembly 10 deployed into its expanded configuration, as shown in FIG. 1C, each of the frame members 14 may move apart from one another such that membrane 20 is distended to form a continuous curved, arcuate, or angled shape which defines the working or surgical theater therein. When frame assembly 10 has been deployed against an epicardial tissue surface to be treated, any number of tools, such as instrument 28 (e.g., RF ablation probe, optical fibers, laser, ultrasound, cryo-ablation probe, microwave ablation probe, graspers, needles, guide-wires, illumination bundles, etc.), may be advanced through one or more working lumens 26 defined through catheter 12 and positioned within the working theater to treat the underlying tissue encompassed within opening 24, as described in further detail below. Additionally and/or alternatively, any number of biological or chemical agents (e.g., saline, biological compounds, fluoroscopy contrast/dyes, etc.) may also be introduced through catheter 12 as well. The interior of the working or surgical theater and the underlying tissue may be visualized directly via a fiberscope 30 or an electronic imager (e.g., CMOS, CCD, etc.) positioned along an interior surface of frame assembly 10 and angled such that the field of view of the imager encompasses the area defined by the assembly 10, also as described in further detail below.

Additional variations of the frame assembly 10 may also encompass conical structures as well as other structures as shown and described in further detail in U.S. patent application Ser. No. 11/259,498 filed Oct. 25, 2005 (U.S. Pat. Pub. 2006/0184048 A1), which is incorporated herein by reference in its entirety.

Figure 2:
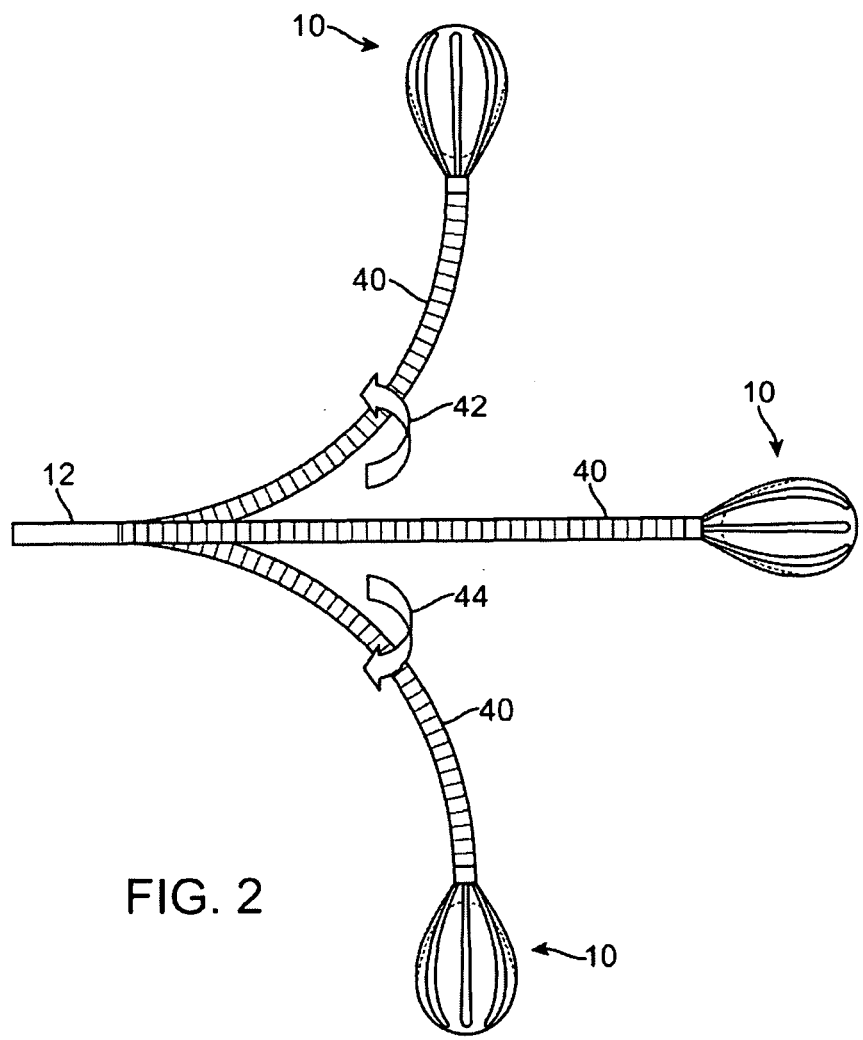
FIG. 2 shows a top view illustrating another example of a device which may be articulated within a plane, e.g., a curved plane, to facilitate manipulation over epicardial tissue.

The treatment system may additionally incorporate a steerable section 40 along catheter 12 proximal of frame assembly 10 to provide for articulation of the device when deployed within the patient body, as shown in the top view of FIG. 2. Manipulation of the steerable section 40 may be controlled by the operator externally of the patient by any number of steering mechanisms to curve frame assembly in either a first direction 42 or second direction 44 opposite to the first direction 42. By optionally incorporating a steerable distal section, frame assembly 10 in either its low-profile or deployed configuration may be articulated within a plane (e.g., a curved plane) or oat-of-plane to position frame assembly 10 along a curved tissue surface, such as the epicardial surface.

Figure 3:
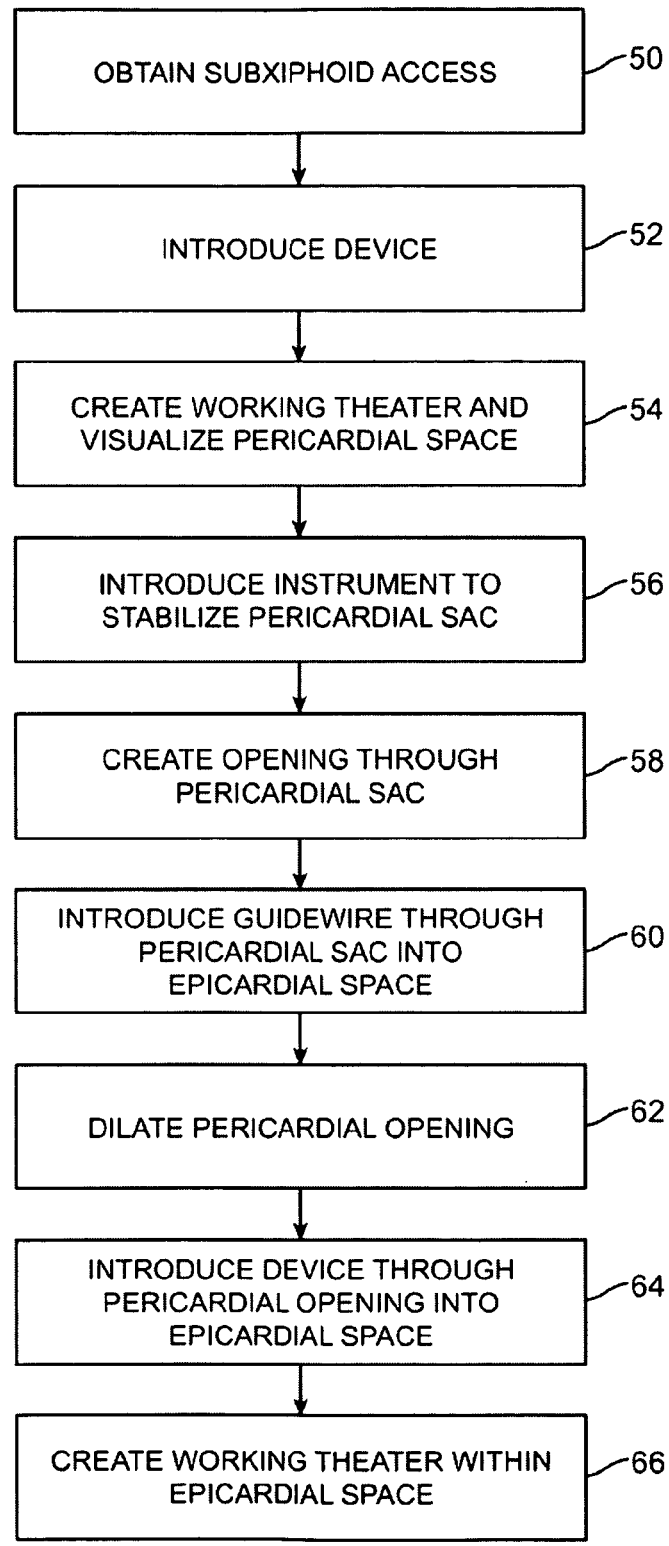
FIG. 3 shows a flowchart illustrating one method for obtaining subxiphoid access to epicardial tissue within a patient.

In use, the device may be advanced through a subxiphoid access point to access the thoracic cavity and the heart in particular. FIG. 3 illustrates an example in a flowchart illustrating one method for obtaining subxiphoid access to the epicardial tissue. Generally, an incision may be made below the xiphoid process overlying the entry site and the linea alba, for instance, may be incised to obtain the subxiphoid access 50. The device in its low-profile tapered delivery configuration may be introduced through the incision 52 and superiorly into the thoracic cavity until the frame assembly 10 is adjacent to the pericardial sac of the heart. Once desirably positioned, frame assembly 10 may be deployed into its open configuration and opening 24 may be placed against the exterior surface of the pericardial sac and the tissue may be directly visualized, either via the fiberscope or electronic imager 54. As the frame assembly 10 is deployed, the surrounding tissue may be retracted by the frame members 14 and the working or surgical theater may be created over the tissue surface.

Once the frame assembly 10 has been deployed over the pericardial tissue, an instrument such as a tissue grasper may be advanced through catheter 12 and into the working theater to grasp a portion of the pericardial tissue to stabilize it 56. A piercing instrument may then be advanced into the working theater through the catheter 12 and an opening may be created through the pericardial sac 58. With the opening formed, a guidewire may be advanced, for example, through the piercing instrument and through the pericardial sac into the epicardial space 60. Once the guidewire has been passed through the opening in the pericardial sac, the piercing instrument may be removed and a dilating instrument may be advanced along the guidewire to dilate the opening 62. Frame assembly 10 may then be collapsed back into its low-profile delivery configuration and advanced along the guidewire and through the dilated pericardial opening until it enters the epicardial space 64 where frame assembly 10 may then be reconfigured back to its deployed configuration. The re-deployment of the frame assembly 10 may retract the pericardial tissue to create the working theater within the epicardial space while directly against the epicardial tissue 66. The entire procedure may be performed while under the guidance of direct visualization through the fiberscope or electronic imager within the working theater to facilitate the access procedure as well as any subsequent treatments.

Figure 4A:
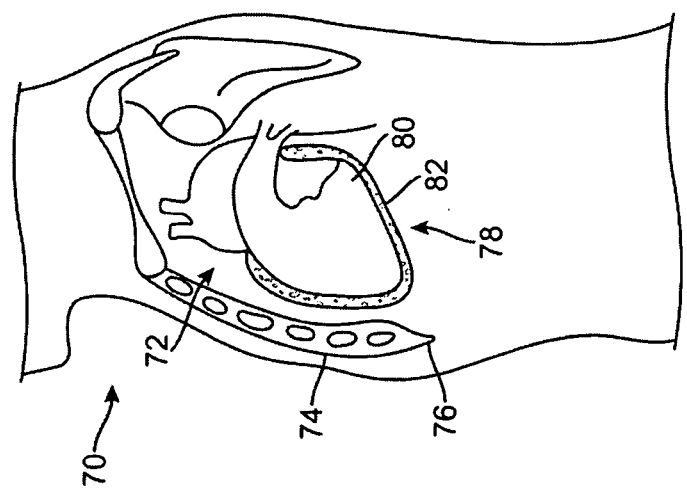
FIGS. 4A to 4D show partial cross-sectional sagittal plane views of a patient's thoracic cavity illustrating one example of subxiphoid introduction via a cannula and the delivery of a reconfigurable device deployed into contact against the pericardial surface.
Figure 4B:
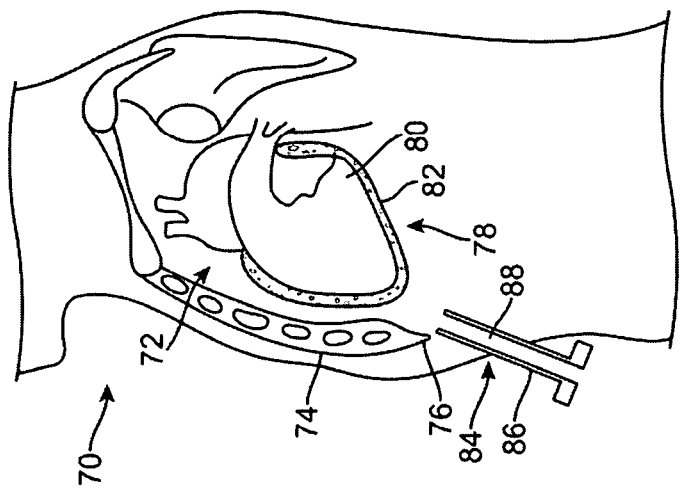

FIGS. 4A to 4D show partial cross-sectional sagittal plane views of a patient's thoracic cavity to illustrate one example of a subxiphoid introduction of the reconfigurable device via a cannula for contact against the pericardial surface. As shown in FIG. 4A, the thoracic cavity 72 of patient 70 is shown with the mediastinum 78 positioned posteriorly to the sternum 74 and xiphoid process 76. The heart 80 may be seen enveloped by the pericardium 82. To access the thoracic cavity 72, an incision 84 may be made (e.g., over the linea alba) inferior to the sternum 74 and a cannula 86 which may be rigid or otherwise flexible may be advanced into the incision 84 at an angle relative to the patient 70 such that the cannula 86 is directed towards the mediastinum 78, as shown in FIG. 4B.

Figure 4D:
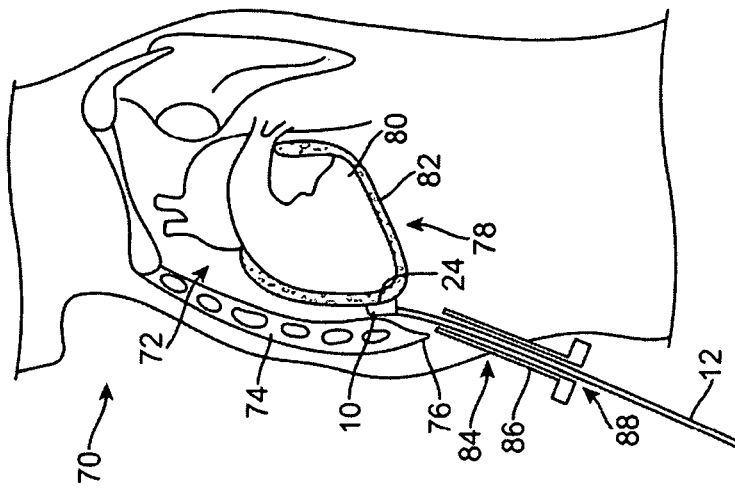
Figure 4C:
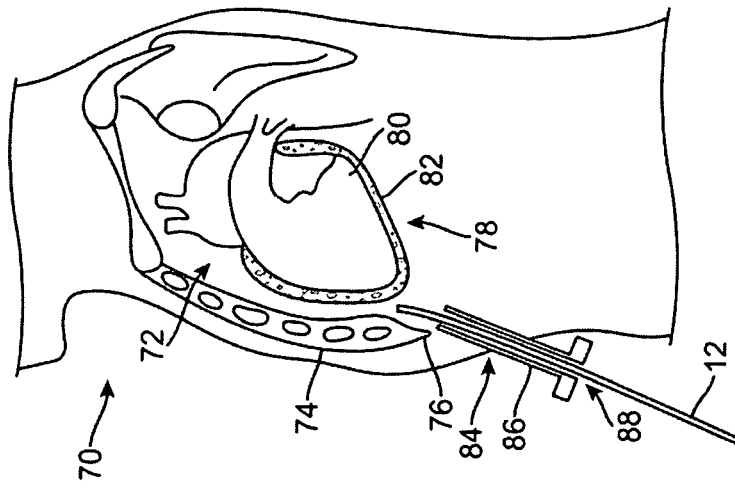

With cannula 86 desirably positioned, catheter 12 with frame assembly 10 in its low-profile delivery configuration may be advanced directly through cannula lumen 88 such that its distal end is advanced subxiphoid into the thoracic cavity 72 and in proximity to the pericardium 82, as shown in FIG. 4C. Alternatively, a blunt dissection, tool may be advanced through cannula lumen 88 to form a path through the tissue to the pericardium 82. The dissection tool may be removed prior to insertion of the catheter 12 and frame assembly 10. In yet another variation, cannula 86 (or an elongate variation thereof) may be advanced directly through the tissue in proximity to the pericardium 82 such that catheter 12 may be introduced through lumen 88 directly into proximity with pericardium 82. In yet another variation, an outer sheath may be advanced through lumen 88 and into proximity with pericardium 82. Frame assembly 10 and catheter 12 may then be advanced through the lumen 88 and outer sheath, which may be manipulated relative to catheter 12.

Once catheter 12 has been advanced subxiphoid posterior to xiphoid process 76 and sternum 74 and into proximity to the surface of pericardium 82, frame assembly 10 may be reconfigured into its deployed configuration and opening 24 may be placed against the surface of the pericardial tissue, as shown in FIG. 4D. With frame assembly 10 expanded, the surrounding tissue may be retracted and the working or surgical theater may be defined over the pericardium 82 while under direct visualization through catheter 12.

Figure 5C:
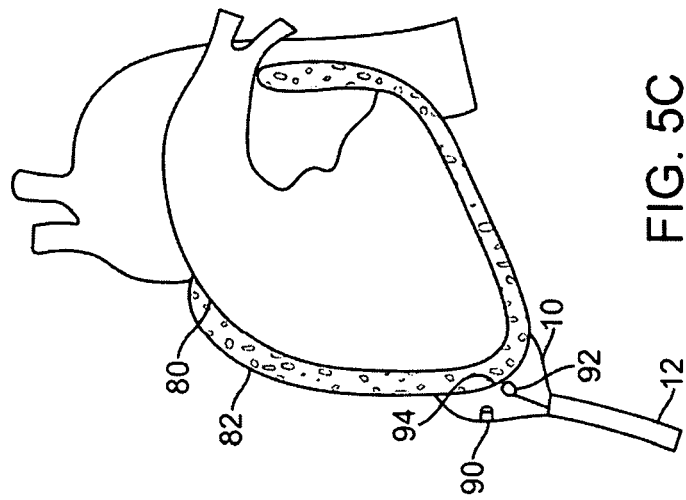
Figure 5B:
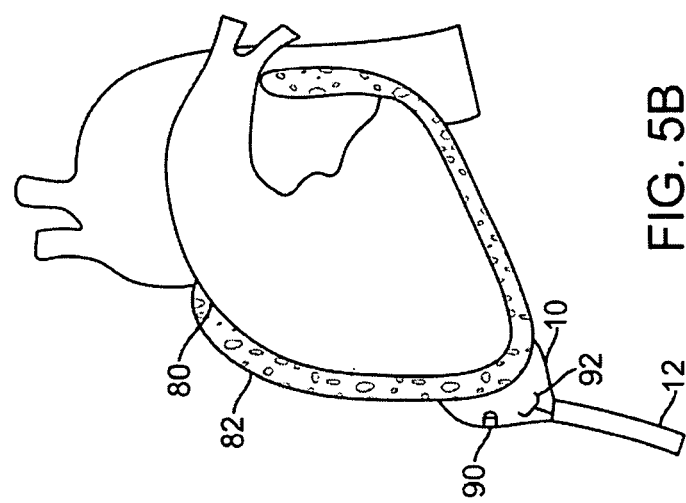
Figure 5A:
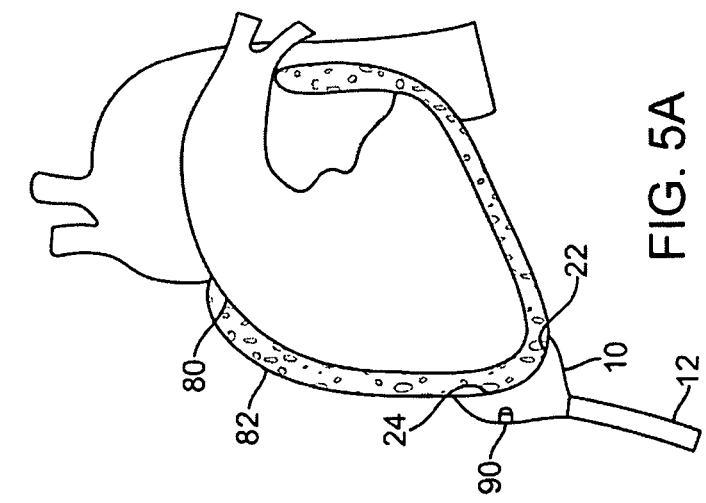

With frame assembly 10 deployed and placed in apposition to pericardium 82, as shown in FIG. 5A, access into the pericardial sac may be achieved while under direct visualization as shown in FIGS. 5B to 5I. As shown in this example, imager 90 (e.g., CMOS, CCD, fiber optic, etc.) may be utilized to view the underlying pericardial tissue contained within the open area 24 and defined by contact edge 22. A fluid, such as saline, may be injected or infused through the catheter 12 and into the working or surgical theater to clear the underlying area of any debris or bodily fluid. A tissue engager 92 (e.g., grasper, corkscrew engager, suction device, etc.) may be advanced through catheter 12 and into the working theater and articulated to engage a portion 94 of the pericardial tissue 82 without pinching or damaging the epicardial surface while under visual guidance, as shown in FIGS. 5B and 5C. While the tissue engager 92 remains engaged to the pericardial tissue, engager 92 may be retracted or otherwise articulated to lift the engaged portion 94 away from the underlying epicardial tissue of the heart 80 to prevent trauma to the underlying epicardial tissue, as shown in FIG. 5D.

Figure 5I:
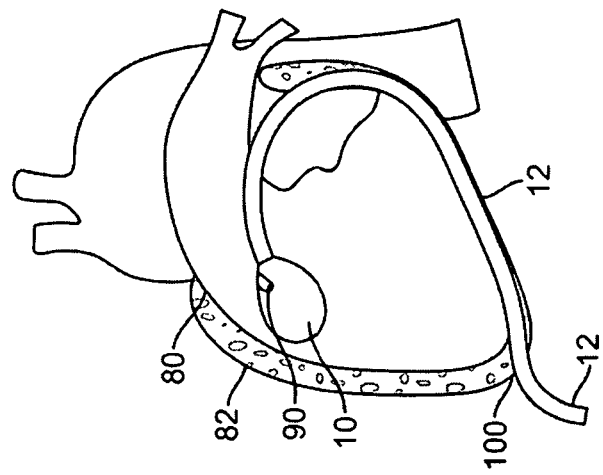
FIGS. 5G to 5I illustrate a further example where a dilating instrument may be advanced along the deployed guidewire to dilate the pericardial opening and allow for the passage of the treatment device through the pericardial opening and into contact along the epicardial tissue surface.
Figure 5H:
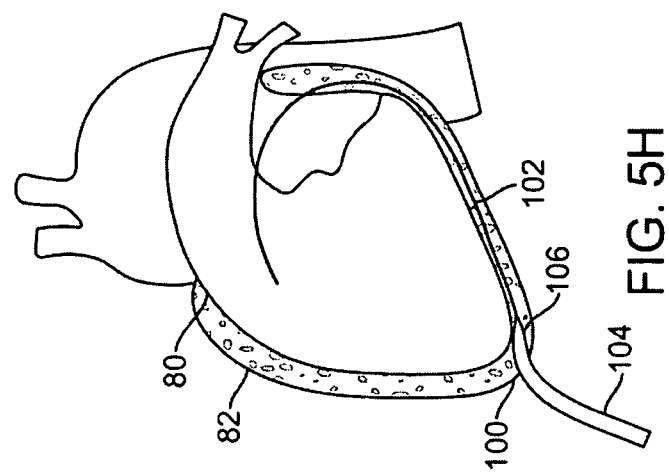
Figure 5G:
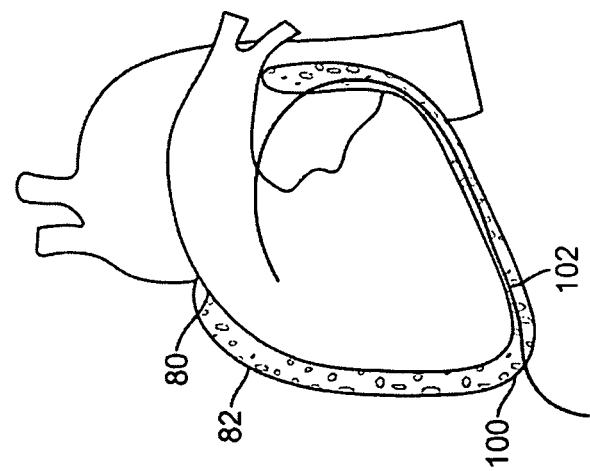

With the engaged pericardial tissue portion 94 retracted from the underlying epicardial tissue, a hollow piercing instrument 96 may be advanced through catheter 12 and into the working theater and while under visual guidance via imager 90, a needle tip 98 of instrument 96 may be safely pierced through the engaged portion 94 and into the pericardial sac to form a pericardial opening 100, as shown in FIG. 5E. A guidewire 102 may then be introduced into the pericardial sac 82 through the piercing instrument 96, as shown in FIG. 5F. With guidewire 102 passing through the pericardial opening 100 and into the epicardial space, frame assembly 10 and catheter 12 may be temporarily removed, as shown in FIG. 5G, and a separate dilating instrument 104 having a tapered dilation tip 106 may be advanced along guidewire 102 to dilate the pericardial opening 100, as shown in FIG. 5H.

Once the opening 100 has been suitably dilated, dilating instrument 104 may be removed and frame assembly 10 and catheter 12 may be re-advanced along guidewire 102 through opening 100 with frame assembly 10 configured in its low-profile shape. Once frame assembly 10 has been introduced within the epicardial space, frame assembly 10 may be reconfigured into its deployed configuration and placed into apposition directly against the epicardial tissue, which may be visualized within the working space while the pericardium 82 and other surrounding tissue is retracted by the expanded frame assembly 10. Frame assembly 10 may then be advanced along guidewire 102 to view and/or treat various regions of the epicardial tissue or the distal portion of catheter 12 may be articulated to move the frame assembly 10 around the epicardial surface, as shown in FIG. 5I.

Figure 6:
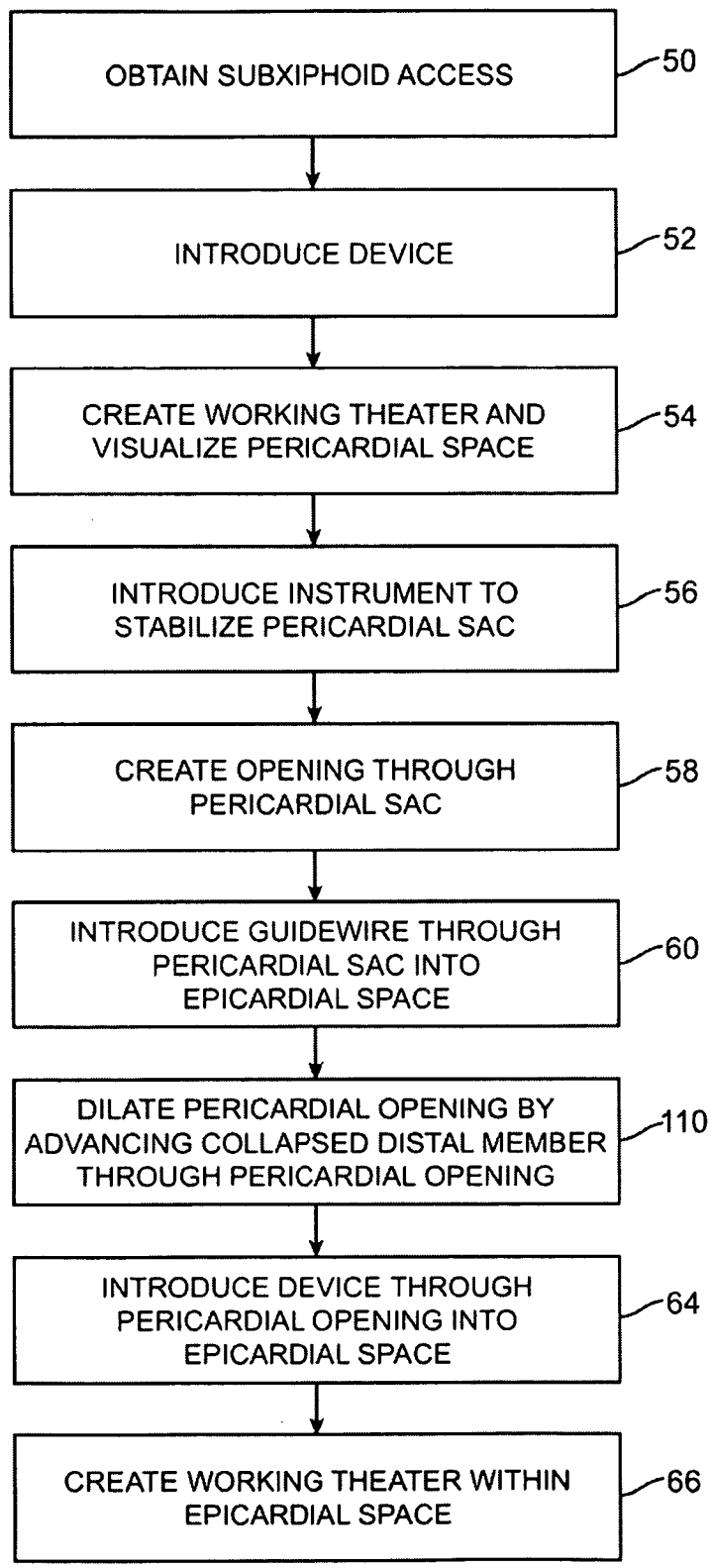
FIG. 6 shows a flowchart illustrating another method for obtaining subxiphoid access to epicardial tissue within a patient utilizing the treatment device also as a dilating instrument.

In another variation, FIG. 6 illustrates an example in a flowchart illustrating another method for obtaining subxiphoid access to the epicardial tissue. Similar to the flowchart shown in FIG. 3 above, subxiphoid access may be obtained and a guidewire may be introduced through the pericardial opening in the same manner. However, rather than utilizing a separate dilating instrument advanced along the guidewire, the frame assembly 10 itself may be advanced along the guidewire in its low-profile configuration and the tapered portion 16 of frame assembly 10 may be used to dilate the pericardial opening by advancing the collapsed tapered portion 16 therethrough 110.

Figure 7A:
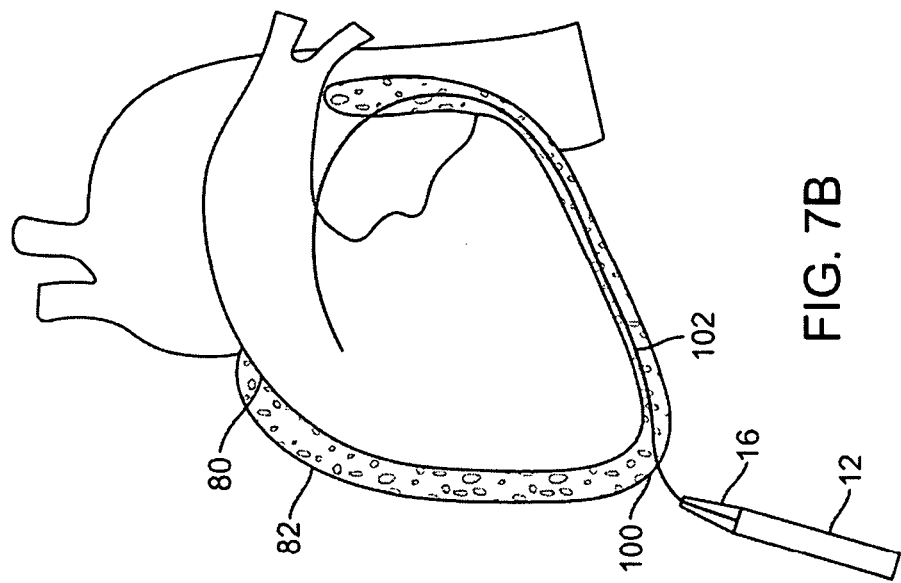
FIGS. 7A to 7D illustrate another example for accessing the underlying epicardial tissue where the treatment device itself may be passed directly through the pericardial opening to dilating the opening.
Figure 7B:
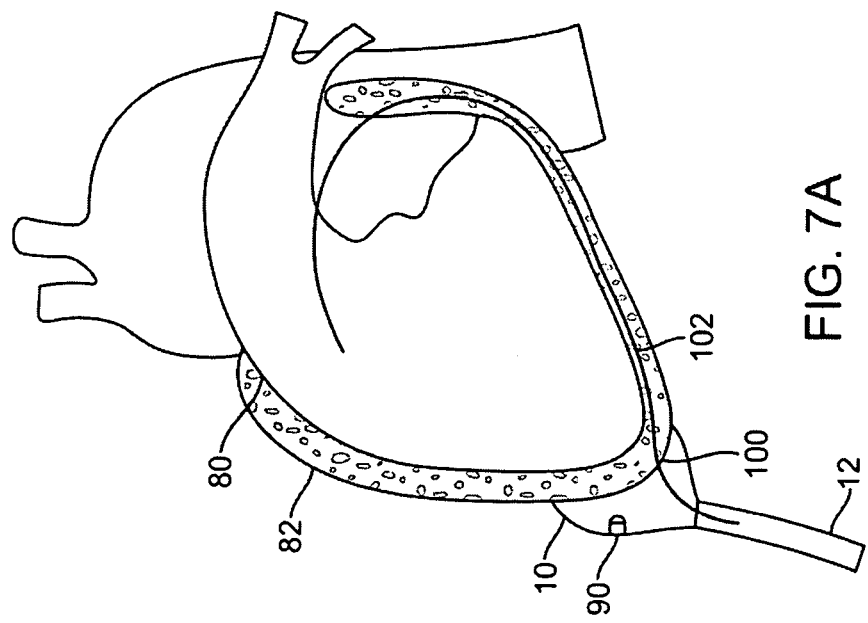
Figure 7D:
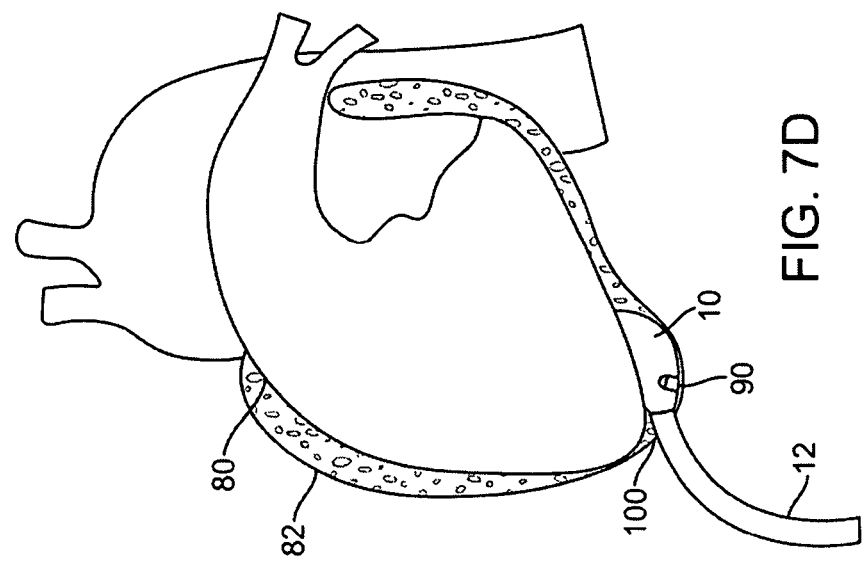
Figure 7C:
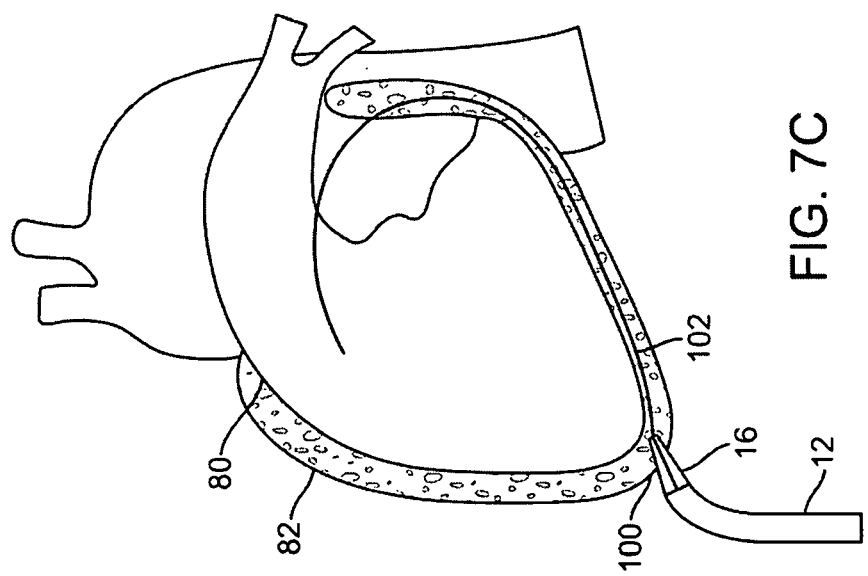

FIG. 7A illustrates the introduction of guidewire 102 through the pericardial opening 100 while under visual guidance via imager 90, as previously described. With guidewire 102 desirably positioned, frame assembly 10 may be collapsed to form the tapered portion 16 while positioned outside of the pericardial opening 100, as shown in FIG. 7B. Catheter 12 may then be advanced distally along guidewire 102 such that tapered portion 16 of frame assembly 10 is used to dilate pericardial opening 100 to allow the passage of frame assembly 10 and catheter 12 therethrough, as shown in FIG. 7C. Once frame assembly 10 has been advanced within the epicardial space, it may be re-deployed to its expanded configuration and placed into contact against the epicardial tissue while under visual guidance from imager 90, as shown in FIG. 7D. Frame assembly 10 may then be repositioned anywhere along the epicardial surface for visualization and/or treatment.

Figure 8A:
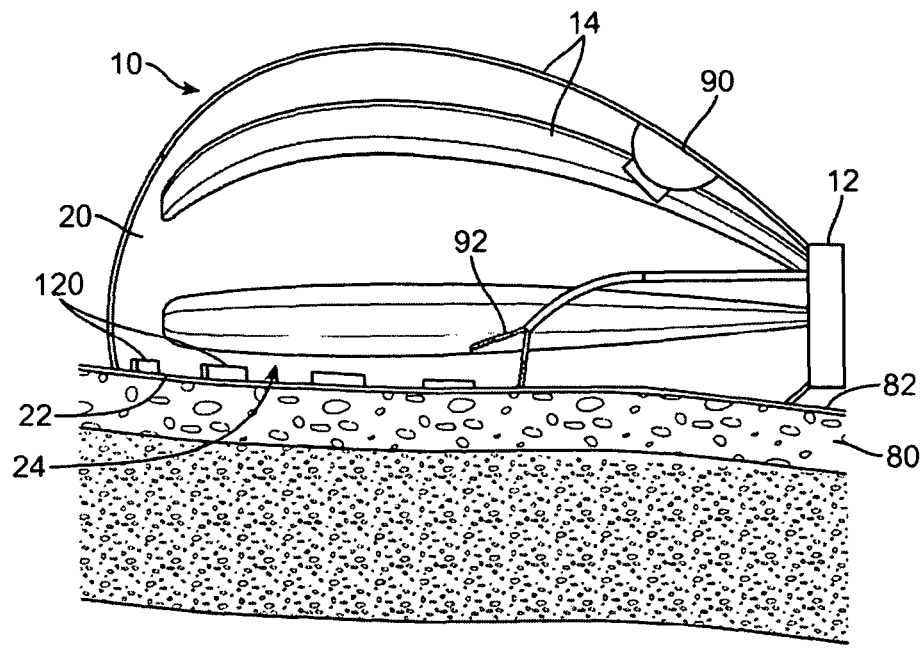
Figure 8B:
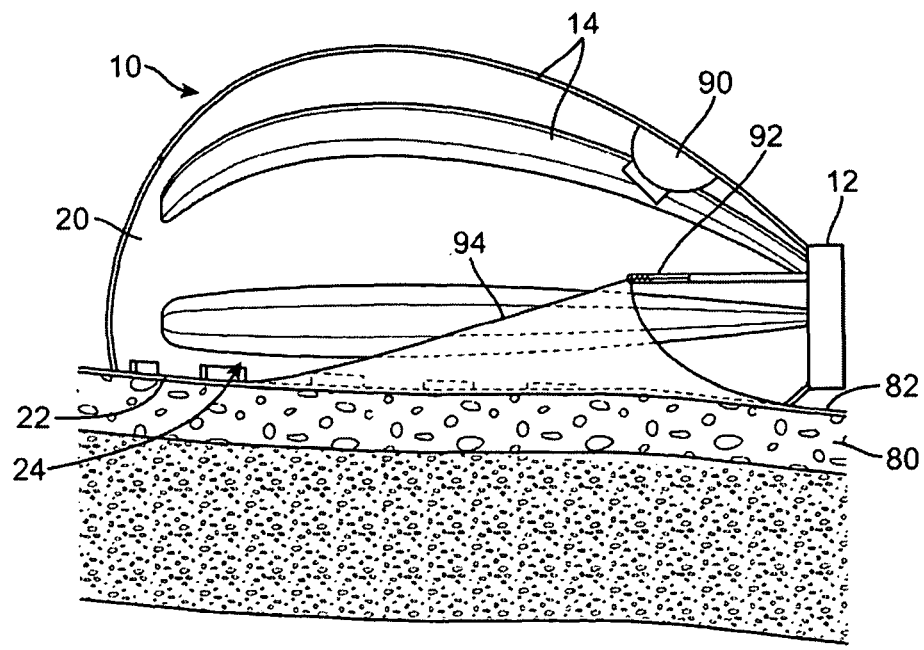

FIGS. 8A to 8D illustrate partial cross-sectional side views showing details of a deployed frame assembly 10 in apposition against a surface of the pericardium 82. As seen in FIG. 8A, deployed frame assembly 10 is expanded, and placed against the pericardial tissue surface while under the visual guidance of imager 90, which in this example is shown attached along an inner surface of membrane 20 and/or frame member 14 and angled off-axis relative to catheter 12. One or more openings or pores 120 may be seen defined along the contact edge 22 surrounding opening 24 in contact against the tissue surface. The openings or pores 120 may be in fluid communication with one another and through catheter 12, e.g., for venting fluids or for suction apposition against the tissue surface to help stabilize the frame assembly 10 against tissue movement such as when the heart beats during a procedure. Tissue engager 92, shown in this example as a tissue grasper, may be advanced distally from catheter 12 and into the working theater where it may be actuated to engage the portion 94 of pericardial tissue, which may be retracted and separated from the underlying epicardial tissue surface, as shown in FIG. 8B.

The piercing instrument 96 may be advanced from an adjacent working channel through catheter 12 below a working channel for tissue engager 92 and advanced distally into the working theater until the piercing tip 98 punctures through the pericardial tissue to form an opening 100, as shown in FIG. 8C. Once the tip 98 is within the pericardial sac, the guidewire 102 may be introduced therein as shown in FIG. 8D and as described above. FIG. 8E illustrates an example where the piercing instrument 96 may be advanced at an angle directly through the pericardium 82 and heart tissue 80 and directly into a heart chamber 122. The frame assembly 10 may be utilized or omitted entirely in this example where the needle tip 98 is advanced through the tissue and into the chamber 122.

Figure 9A:
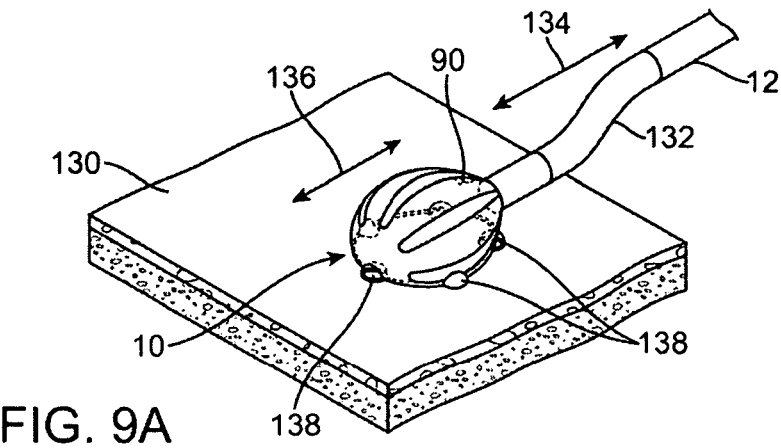
FIGS. 9A to 9C show perspective views of another variation of the treatment device which may be configured to temporarily engage against the epicardial tissue surface to stabilize the device against movement of the heart, e.g., when beating.
Figure 9B:
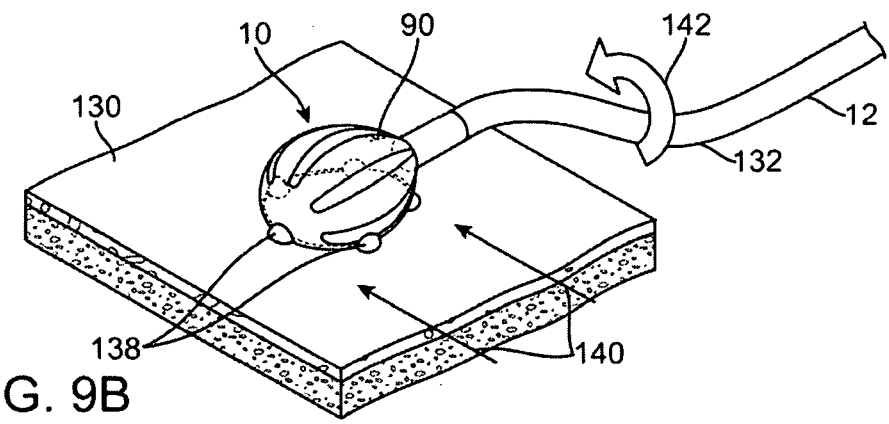
Figure 9C:
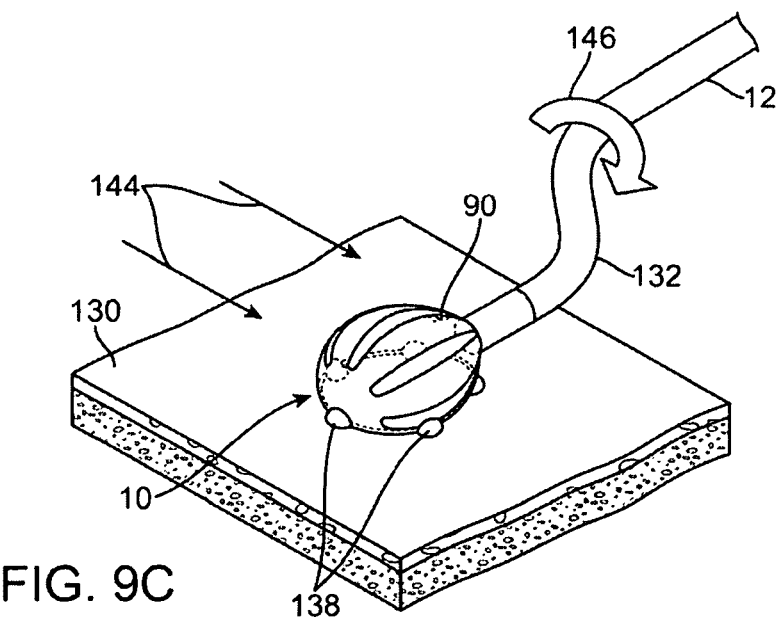

In yet another variation, the frame assembly 10 may further include one or more defined suction ports 138 positioned around the opening 24 to facilitate temporary securement or stabilization of the device against the tissue surface despite movement of the tissue such as when the heart beats. Generally, the frame assembly 10 may comprise an attachment portion 136 while the catheter 12 may include a flexible and/or elastic portion 134 to accommodate for the difference in relative movement between the frame assembly 10 and the catheter 12. As shown in the perspective views of FIGS. 9A to 9C, deployed frame assembly 10 may be seen expanded and positioned along epicardial tissue surface 130. Frame assembly 10 may include the one or more defined suction ports 138 positioned around the opening 24 such that when suction is drawn through catheter 12 and suction ports 138, frame assembly 10 may be temporarily adhered to the underlying tissue surface 130. Because of the inherent tissue movement, such as when the heart beats, flexible segment 132 may allow for relative motion as illustrated in FIGS. 9B and 9C. As the frame assembly 10 is moved between a first direction 140 of tissue movement and a second direction 144 of tissue movement opposite to the first direction 140, flexible segment 132 is shown to flex and bend allowing for a relative movement 142 and a relative movement 146, respectively, such that damage or trauma to surrounding tissue is prevented or inhibited. The flexible segment 132 may be comprised of any number of elastic materials, e.g., medical grade elastomers such as silicone or polyurethane, etc.

Moreover, including flexible segment 132 may also enable image stabilization within the working or surgical theater when visualizing a moving epicardial surface. As the distal hood member is attached and moving together with the beating heart, relative motion of the synchronized objects may allow visualized images of the moving epicardial surface to appear stationary.

Figure 10A:
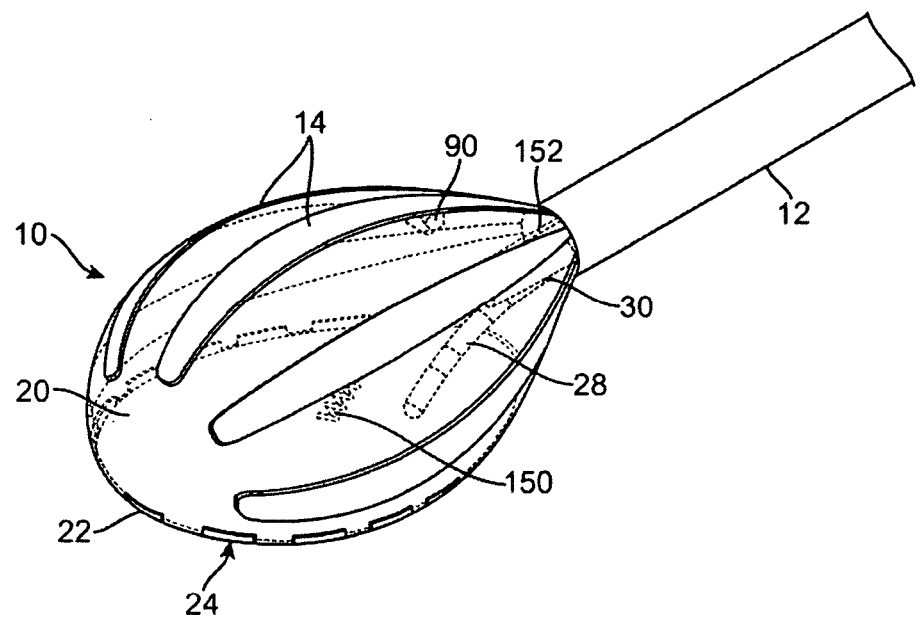
FIGS. 10A and 10B show perspective and partial cross-sectional side views, respectively, of another variation of the device with one or more instruments advanced through the catheter and into the surgical field of the device.
Figure 10B:
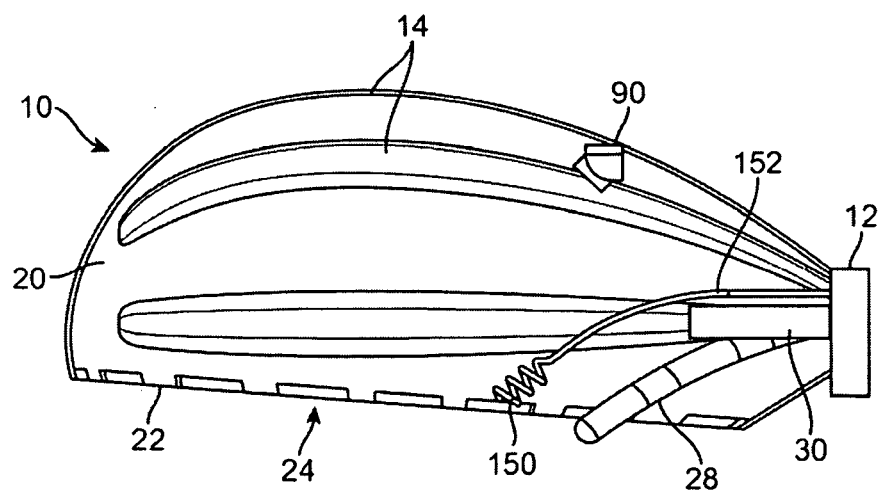

In illustrating the utility and flexibility of the system for use in different procedures, various instruments are shown advanced through catheter 12 and positioned within the working or surgical theater in the perspective and partial cross-sectional side views of FIGS. 10A and 10B. This example shows an ablation probe 28 (e.g., RF, cryo, laser, ultrasound, microwave, etc.), fiberscope 30 (as well as electronic imager 90), and epicardial biventricular pacing lead 150 attached to a lead connector 152 as examples of the various instruments which may be positioned through the working lumens of catheter 12. Alternative instruments may also include ECG pacing or sensing, graspers, needles, saline irrigation, contrast injection, tissue closure implants, tissue sealing tools, stents, etc.

Moreover, examples of various procedures that can be performed with the system may include, but are not limited to, pacing lead implantation, ablation of cardiac arrhythmias, left atrial appendage closure, percutaneous septal defect closure, percutaneous valve replacement, tamponade repair, epicardial ECG pacing and mapping, etc.

Figure 11A:
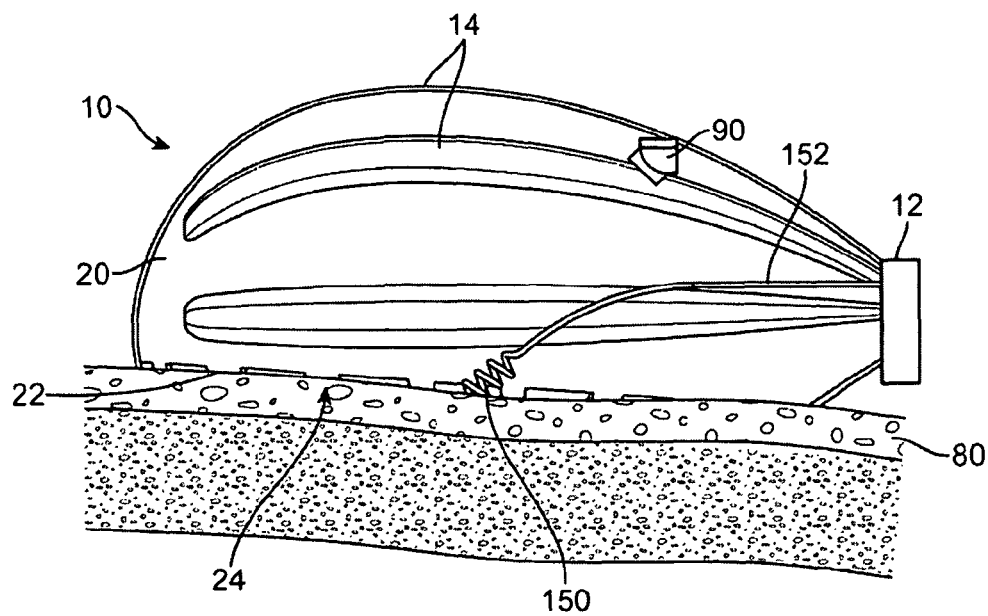
FIGS. 11A and 11B show side views of a treatment device having an epicardial biventricular pacing lead advanced into the surgical field and subsequently engaged to the underlying epicardial tissue.
Figure 11B:
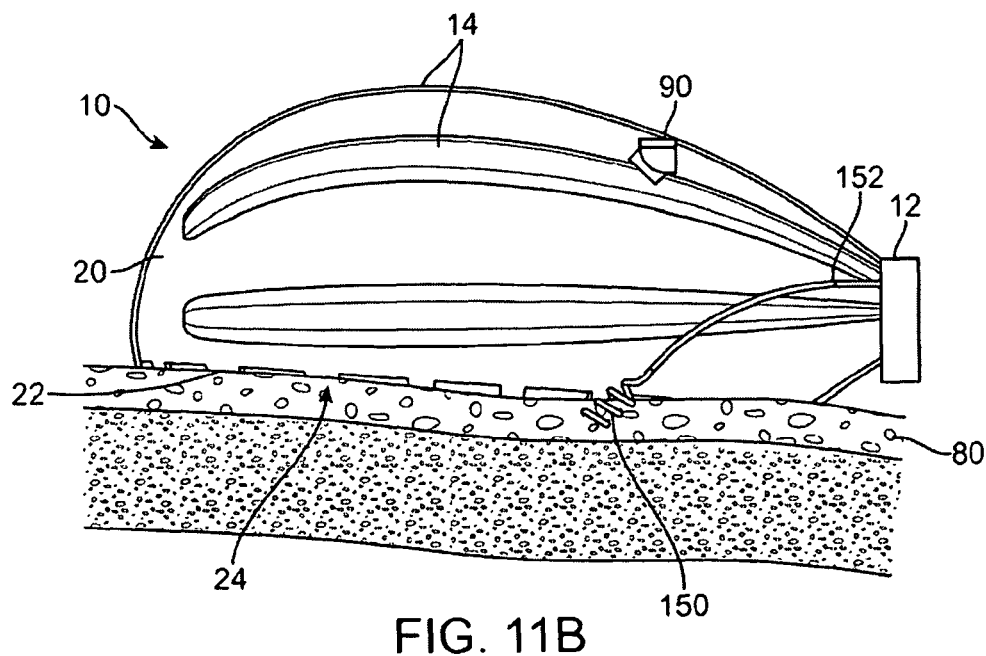

FIGS. 11A and 11B illustrate an example of improved efficiency and efficacy of yet another epicardial treatment when performed under direct visualization. In a typical procedure in implanting a pacing lead, although the pacing lead 150 placed might provide good electrical contact based on ECG data, die same lead 150 might have been attached with poor mechanical contact which ECG or fluoroscopy data may not easily detect thus leading to ineffective therapy and treatment. FIG. 11A shows an example in the partial cross-sectional side view of the device where ineffective placement of an epicardial pacing lead 150 may be detected under direct visualization from imager 90. Thus, having direct visual confirmation may ensure both mechanically and electrically well-placed leads or other treatments performed epicardially, as shown in FIG. 11B.

Figure 12:
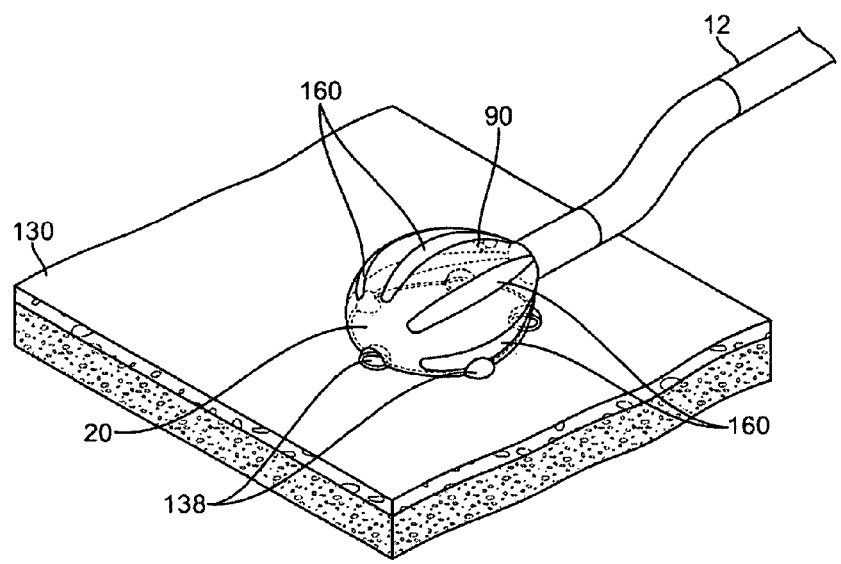
FIG. 12 shows a perspective view of another variation where the barrier or membrane as well as the frame members may be fabricated as a translucent and/or transparent device.

In yet another variation, FIG. 12 shows a perspective view of a frame assembly 10 where the entire assembly 10 may be made from fully transparent and/or translucent frame members 160. Such materials may include, e.g., polyurethane, polycarbonate, etc. and may allow for visualization of tissue with imager 90 or a fiberscope positioned within catheter 12 even when the frame members 160 are in their collapsed configuration. This can be useful particularly when rapid dilation is performed with a collapsed frame assembly, as described above, as the surgeon may be able to see through the collapsed frame assembly to avoid tissue damage or perforation during the dilation process.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method for accessing a tissue region, comprising:
    advancing an elongate catheter into a body in proximity to the tissue region;
    reconfiguring a frame assembly extending from a distal end of the catheter from a low-profile delivery configuration to a deployed configuration such that a working theater is defined which is in communication with the catheter and which has a contact edge defining a lateral opening off-axis relative to a longitudinal axis of the catheter;
    positioning the opening against the tissue region underlying the working theater;
    retracting surrounding tissue via the frame assembly; and
    engaging a portion of pericardial tissue within the working theater and lifting the pericardial tissue from epicardial tissue.

2. The method of claim 1 wherein advancing comprises introducing the catheter through a subxiphoid access point.

3. The method of claim 2 further comprising advancing the catheter into the thoracic cavity posterior to a xiphoid process and into proximity with a pericardium.

4. The method of claim 1 wherein reconfiguring further comprises visualizing the underlying tissue within the working theater via an imager positioned within an interior of the theater.

5. The method of claim 1 wherein reconfiguring further comprises adhering the frame assembly to the underlying tissue region such that the assembly is stabilized with respect to the tissue.

6. The method of claim 1 further comprising forming a pericardial opening through the pericardial tissue.

7. The method of claim 6 further comprising passing a guidewire through the pericardial opening.

8. The method of claim 7 further comprising reconfiguring the frame assembly into its delivery configuration and advancing the assembly through the pericardial opening.

9. The method of claim 8 further comprising reconfiguring the frame assembly into its deployed configuration and into contact against epicardial tissue.

* * * * *